United States Patent [19]

Skov

[11] 4,298,694

[45] Nov. 3, 1981

[54] PROCESS AND A PLANT FOR PREPARING A GAS RICH IN METHANE

[75] Inventor: Allan Skov, Lyngby, Denmark

[73] Assignee: Haldor Topsøe A/S, Lyngby, Denmark

[21] Appl. No.: 99,361

[22] Filed: Dec. 3, 1979

[30] Foreign Application Priority Data

Dec. 12, 1978 [DK] Denmark .............................. 55711/78

[51] Int. Cl.$^3$ .............................................. C07C 1/04
[52] U.S. Cl. .................................... 518/704; 518/706; 518/707; 518/712; 48/197 R; 422/189
[58] Field of Search ....... 260/449 S, 449 M, 449.6 M; 48/197 R

[56] References Cited

U.S. PATENT DOCUMENTS

| | | | |
|---|---|---|---|
| 3,511,624 | 5/1970 | Humphries et al. | 260/449 M |
| 3,888,043 | 6/1975 | Child et al. | 260/449.6 M |
| 3,922,148 | 11/1975 | Child | 260/449 M |
| 4,012,404 | 3/1977 | Liebgott | 48/197 R |
| 4,016,189 | 4/1977 | Muller et al. | 260/449 X |
| 4,061,475 | 12/1977 | Moller et al. | 48/197 R |
| 4,064,156 | 12/1977 | McRobbie | 260/449 S |
| 4,123,448 | 10/1978 | Kleinpeter | 260/449 S |
| 4,124,628 | 11/1978 | McRobbie | 260/449 X |

Primary Examiner—Howard T. Mars
Attorney, Agent, or Firm—Lawrence Rosen

[57] ABSTRACT

The invention relates to an improved catalytic methanation process wherein a feed gas containing predominantly hydrogen and being rich in carbon oxides (CO and/or $CO_2$) is divided into two part streams of which the first is methanated partially in an adiabatic methanation reactor by a methanation catalyst whereafter the effluent from the adiabatic methanation reactor is united after cooling with the second feed gas part stream and the thus-combined stream is methanated in a cooled methanation reactor by a methanation catalyst, preferably the same as that used in the adiabatic methanation reactor. It is possible, but not always necessary, to recycle part of the recycle gas to the adiabatic methanation reactor to keep the temperature therein at a moderate level. The process is useful in connection with transport of energy from a nuclear reactor. It is advantageous because it can be operated to produce superheated steam, for use, e.g. for producing electricity, in connection with the cooling of the effluent from the adiabatic reactor, whereby energy losses can be reduced to a very low level; and because the amount of recycle gas is reduced, possibly to nil, whereby energy is saved.

6 Claims, 2 Drawing Figures

PROCESS AND A PLANT FOR PREPARING A GAS RICH IN METHANE

The present invention relates to a process for preparing a methane-rich gas mixture by catalytic treatment at elevated temperature and pressure of a feed gas which contains hydrogen and is rich in carbon oxides.

BACKGROUND OF THE INVENTION AND PRIOR ART

The methanation proceeds rapidly to equilibrium in the presence of a catalyst, according to one or both of the reactions below, the energy conversion of which is referred to 1 bar and 0° C.

$$CO + 3H_2 \rightleftharpoons CH_4 + H_2O \quad \Delta H = -205.15 \text{ kJ/mol} \quad (1)$$

$$CO_2 + 4H_2 \rightleftharpoons CH_4 + 2H_2O \quad \Delta H = -163.91 \text{ kJ/mol} \quad (2)$$

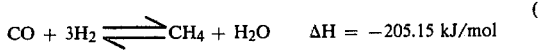
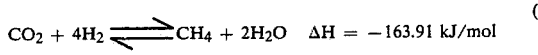

Simultaneously an equilibrium between carbon monoxide and carbon dioxide will set itself as stated below:

$$CO + H_2O \rightleftharpoons CO_2 + H_2 \quad \Delta H = -41.24 \text{ kJ/mol} \quad (3)$$

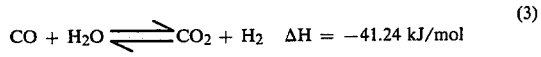

Methanation of gases containing small amounts of carbon oxides has been known for a long time. As an example may be mentioned ammonia plants wherein the ammonia synthesis gas, which mainly contains hydrogen and nitrogen, is subjected to a methanation before the proper ammonia synthesis. By the methanation the carbon oxides, which are poisonous to the ammonia catalyst, are converted into methane.

In recent years the methanation of gases containing larger amounts of carbon oxides has been the subject of great interest. Firstly there is an increasing need of preparing methane-rich gases as substitute for natural gas (Substitute Natural Gas, SNG). Secondly, the methanation process is convenient in connection with the transport of chemically bound energy.

Since the reserves of natural gas are limited and since it involves ever increasing costs to win natural gas, it has been attempted in recent years to improve the methods of preparing substitute gases from cheap carbonaceous raw materials such as heavy fuel oils and naturally occurring coal. A number of processes for the gasification of solid and liquid carbonaceous materials are commercially available to-day. These processes have in common that the carbonaceous material is reacted under elevated pressure and temperature with atmospheric air and/or pure oxygen and/or steam. The composition of the product gas from the gasification plant varies from process to process but it predominantly consists of carbon oxides, hydrogen, steam, lower hydrocarbons, mainly methane, and possibly nitrogen. Additionally, the sulfur contents of the raw material will be converted into hydrogen sulfide and/or carbonyl sulfide. Apart from this there will be formed small amounts of low molecular weight organic compounds, i.a. formic acid and hydrogen cyanide. Before this product gas from the gasification plant can be methanated it will be necessary to subject it to various treatments such as removal or conversion of such sulfur compounds and other undesired compounds. For a review of the various gasification processes reference is made to "Ullmanns Encyklopädie der Technischen Chemie", 4th impression, vol. 14, 1977.

In connection with the utilization of nuclear power a new use of the methanation process has become of immediate importance. As is apparent from reaction equations (1) and (2), the formation of methane from carbon dioxides and hydrogen is connected with heat generation and conversely the reaction with steam, the so-called steam reforming, is dependent on the intake of heat. In accordance with this, the heat generated in a nuclear reactor may be used to form carbon oxide (CO and/or $CO_2$) and hydrogen from methane. In this way the thermal energy is bound and the gases can be transported through pipelines to the places where one wants to utilize this energy. There a methanation is then carried out and the heat generated can be used for electricity production, house warming and other purposes. For a more detailed elucidation of this tropic reference is made to the paper "Transport von Kernwärme mittels chemisch gebundener Energie" by U. Boltendahl et al., published in gwf-gas/erdgas 117 (1976) H. 12, pp. 517-522.

Methanation may be carried out in a number of reactor types differing in principle. The abovementioned methanation of ammonia synthesis gas containing small amounts of carbon oxides is carried out in adiabatic reactors. Such reactors are characterized in general by their simple construction which renders the filling up of catalyst a simple operation. The control of an adiabatic reactor is likewise comparatively simple since the amount of heat evolved is low because of the low content of carbon oxides.

By the methanation of gases having high contents of carbon oxides the amount of heat generated in accordance with the reaction equations (1) and (2) will be so considerable and the temperature thereby so high that the catalyst in an adiabatic reactor may be destroyed, and possibly even the reactor may be damaged. One way of solving this problem involves the cooling and recycling from the outlet of the reactor of part of the methanated gas. Such a process has been described in UK Pat. No. 1,516,319 and U.S. Pat. No. 4,130,575. It is a drawback of this process that considerable amounts of energy are used for the recycling, whereby the total useful effect of the process is reduced.

Another drawback of methanation in an adiabatic reactor is that the enthalpy change by exothermic reactions in accordance with the principle of Le Chatelier will adjust the chemical equilibrium on a gas composition which is disadvantageous in comparison with that desired since the equilibrium concentration of the desired reaction product (methane) decreases with increasing temperature.

Another type of reactor, used in connection with exothermic processes, is the cooled reactor. This reactor most often is constructed as a bundle of parallel tubes in a pressure shell. The catalyst may either be placed in the tubes with the cooling medium round all of the tubes, or vice versa. As cooling medium a large number of liquids with suitable boiling points may be used. Most often one of the heat transfer media called "Dowtherm ®" is used. The advantages in using a cooled reactor for methanation i.a. are that the needful amount of catalyst is smaller and that it is possible because of the lower discharge temperature from the reactor to obtain a greater concentration of the desired reaction product (methane) in the outflowing gas from the reactor. When water is used as cooling medium in a cooled reactor, it is a general disadvantage that the steam produced is saturated and therefore it is usable in steam turbines only after having been superheated.

OBJECT OF THE INVENTION

It is the object of the invention to provide a process for methanation in which on one hand one reduces the inner energy consumption attached to the methanation in an adiabatic reactor by completely avoiding recycling or reducing the relative amount of gas recycled and thereby obtains an increased useful effect, and on the other hand one carries out the methanation in such manner that the heat of reaction from the adiabatic reactor is utilized for superheating saturated steam produced in a cooled reactor, whereby there is obtained superheated steam which is usable for driving a steam turbine, for example for electricity production.

SUMMARY OF THE INVENTION

The invention relates to a process for preparing a combustible gas mixture rich in methane by the catalytic treatment as elevated temperature and pressure of a feed gas which contains hydrogen as the predominant component, is rich in carbon oxides and optionally contains steam and/or gases inactive relative to the reactions involved such as nitrogen and possibly the inert gases. The above object is achieved in such a process if the feed gas is divided into two part streams each containing 30–70% by volume of the total feed gas stream, the first of these part feed gas streams is subjected to a catalytic methanation in at least one adiabatic methanation reactor and then cooled, and the second part feed gas stream is mixed with the cooled outlet stream from the adiabatic methanation reactor whereafter the thus-combined stream is subjected to a catalytic methanation in at least one cooled methanation reactor and the outlet stream from this recovered as a product gas which optionally is subjected to further treatments not pertinent to the present invention.

Accordingly, the process of the invention consists of the steps of (a) dividing the feed gas into two streams, a first feed gas part stream comprising 30–70% by volume of the total feed gas stream and a second feed gas part stream comprising the remainder of the feed gas, (b) subjecting the first feed gas part stream to a catalytic methanation in at least on adiabatic methanation reactor containing a bed of a methanation catalyst, (c) cooling the outlet gas stream from the adiabatic methanation reactor to 250°–400° C., (d) mixing the cooled outlet stream of step (c) with the second feed gas part stream to form a combined stream, (e) subjecting the combined stream from step (d) to a catalytic methanation in at least one cooled methanation reactor containing a bed of a methanation catalyst, and (f) recovering the outlet gas from the cooled methanation reactor totally or partially as a product gas for use or further treatment.

Figure 1:
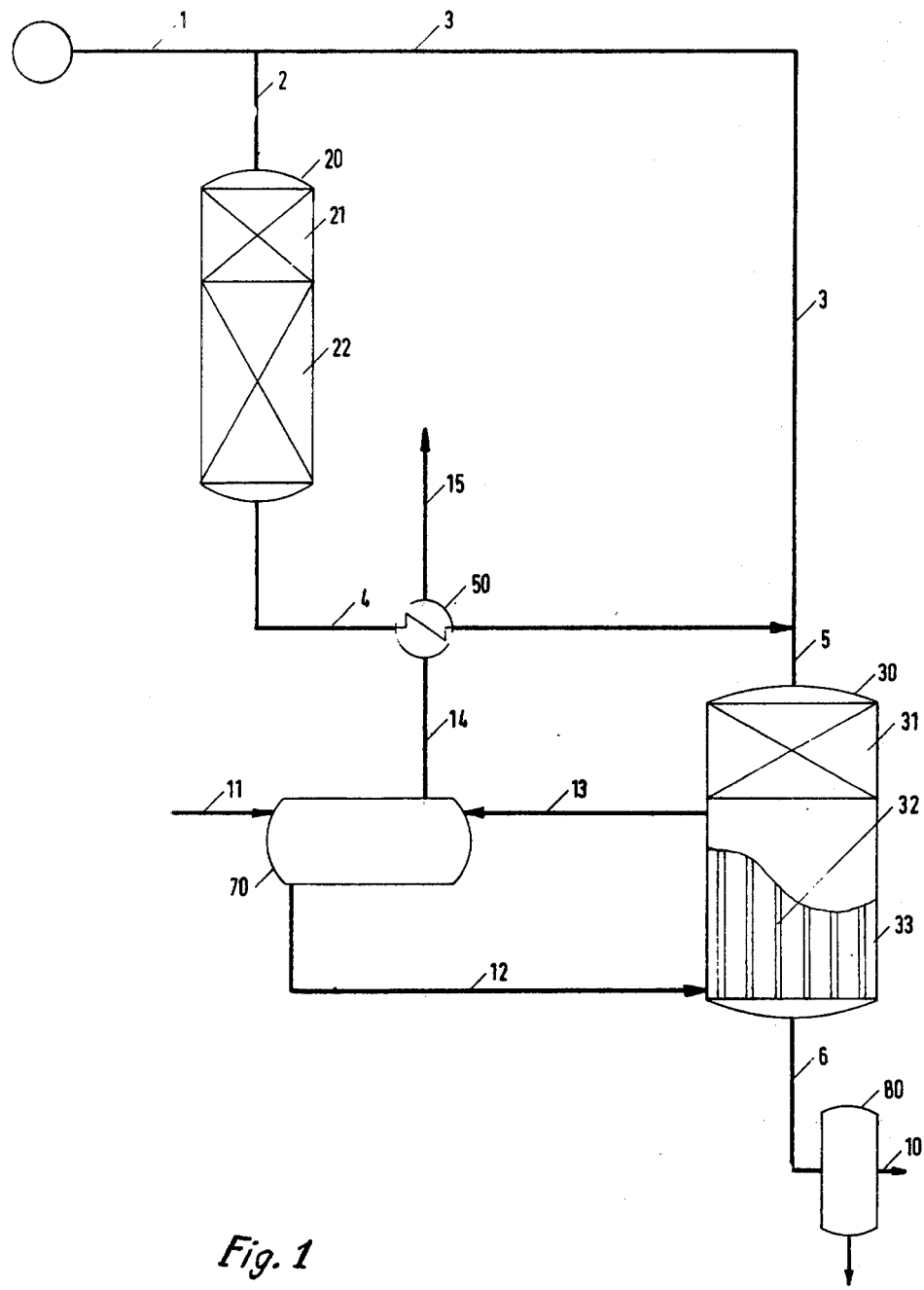
FIG. 1 shows a flow diagram for one embodiment of the process according to the invention, not using recycling of any part of the product gas and FIG. 2 a flow diagram for the preferred embodiment of the process in which a comparatively small part of the product gas is recycled.

The specific constructions and relative positions of reactors, heat exchangers, compressors and steam system as well as the specific temperature, pressure and flow control techniques employed do not form part of the invention. Various valves, pumps, regulators and other standard equipment necessary to carry out the invention in practice have not been shown on the drawing. The use and function of such equipment is well-known and the omission thereof on the drawing means a simplification which facilitates the understanding and the characteristic features of the process of the invention.

DETAILED DESCRIPTION OF THE VARIOUS EMBODIMENTS OF THE INVENTION

Hereinbefore a distinction is drawn between feed gas mixtures having a high and feed gas mixtures having a low content of carbon oxides (carbon monoxide and/or carbon dioxide, normally most of the former). The present invention only aims at carbon oxide-rich gases, i.e. feed gas mixtures having a high content of one or both carbon oxides. By "rich in carbon oxides" is not meant that the feed gas mixture contains carbon monoxide and possible also carbon dioxide as the quantitatively largest component, since hydrogen will normally be quantitatively by far the largest component in the feed gas mixture, but merely that the contents thereof are high in comparison with feed gas mixtures having low contents (e.g. 1 or a few percent) of carbon oxides. The feed gas mixture for the process according to the present invention thus shall have a content of at least 10% by volume of carbon oxides but the content may be well above this amount.

Altogether, as is well-known and, incidentally, as appears from the references mentioned above there can be considerable variation in the composition of gas mixtures used for methanation according to source of the gas mixture, the pre-treatment (purification) to which it has been subjected and the demands made at the methanated gas. Relevant parameters are, i.a., regulations concerning and demands on the methanated gas, minimum calorific value and contents of poisonous components.

It is therefore to be emphasized that the process of the invention is not linked to any particular feed gas composition apart from the fact that it must have a high content of carbon oxides, but on the contrary that one of the advantages of the process precizely as its flexibility regarding the composition of the methanable gas. This flexibility later in the specification is demonstrated by a number of Examples.

In an embodiment of the process of the invention, preferred in certain cases, the outlet stream from the cooled methanation reactor, i.e. from step (e), is divided into a product stream and a recycle stream. The latter, optionally after cooling, is mixed with the first feed gas part stream before it is fed to the adiabatic methanation reactor, in such an amount that the ratio of recycle stream to feed gas part stream is between 0.05:1 and 1.5:1, preferably between 0.1:1 and 0.9:1. Hereby it is possible to ensure that the temperature in the adiabatic methanation reactor will rise to between 500° C. and 800° C.

When combining a recycle stream from the cooled methanation reactor with the first feed gas part stream, the former will in most cases be cooled before it is united with the part strem to the adiabatic reactor. Dependent on the feed gas composition and the desired composition of the product gas one can sometimes omit to cool the recycle stream whereby a simplification of the plant is obtained by leaving out a heat exchanger. When cooling is applied, the recycle gas should be cooled to 200°–400° C., preferably 250°–350° C.

However, as mentioned it is a particular advantage of the invention that the recycling can either be avoided altogether or reduced strongly in comparison with known methanation processes. When recycling is used in the preferred embodiment, the ratio recycle stream of product gas from the cooled methanation reactor to feed gas part stream as stated is as low as between 0.05 to 1.5, preferably between 0.1 and 0.9; in Examples 2–8 hereinafter the said ratio is between 0.15 and 0.65. Because of this low recycle ratio there is obtained a considerable saving of energy in comparison with known methanation processes where the recycle ratio usually is around 3:1 or even higher and in certain cases above 100:1.

As stated hereinbefore the methanation process is catalytic and catalyst is present in both of the reactors. The invention is not linked to the use of any particular catalyst. The methanation reaction is catalyzed by a number of metals such as cobalt, rhodium, palladium, platinum, ruthenium and nickel. For economic reasons a catalyst consisting of reduced nickel is preferred as a rule, i.e. metallic nickel on a catalyst carrier. Suitable catalysts are described in British Pat. Nos. 1,505,254 and 1,546,774. Conveniently, the same methanation catalyst is used in both of the reactors but the conditions of operation may prompt the use of two or more different catalysts. Thus, it is necessary to use a particularly heat-resistant catalyst in the adiabatic methanation reactor when the latter is operated at temperatures substantially above 700° C.

The cooling medium in the cooled methanation reactor normally will be boiling water although also others may come into consideration. If the cooling medium is water, the saturated steam produced in the cooled methanation reactor may conveniently be used for cooling the gas stream leaving the adiabatic methanation reactor. Hereby one utilizes in a constructively simple way the abovementioned advantage of the process of the invention that superheated steam may be formed, e.g. for production of electricity. At the same time, the gas stream from the adiabatic methanation reactor is cooled to 250°–400° C., preferably 300°–350° C.

The process of the present invention has the great advantages that practically all of the heat of reaction can be utilized for producing superheated steam, and that that superheated steam may be produced within the ranges of pressure and temperature which are convenient for the production of electricity. This flexibility is caused by the possibility of varying the ratio of feed gas part stream conveyed to the adiabatic methanation reactor and feed gas part stream conveyed to the cooled methanation reactor. If the part stream conveyed to the adiabatic reactor is increased, there will be an increased amount of heat of reaction available for superheating the steam and accordingly this obtains a higher temperature. If on the other hand an increased amount is conducted to the cooled reactor, the amount of heat available for superheating the steam will decrease and the latter will obtain a lower temperature. The ultimate determination of relative amounts of the two feed gas part streams will, apart from the requirements set by a given specification on the superheated steam, depend upon a number of other factors such as the feed gas composition, temperature and pressure in the methanation process, etc.

Superheated steam for the production of electricity normally will have a pressure of 90–160 atm. abs. and a temperature of 500°–550° C. Normally, such steam can be obtained in the present process with a distribution of the feed gas stream between the two reactors within the range of from 3:7 to 7:3, preferably from 4:6 to 6:4. In the Examples hereinafter the ratio of distribution is between 64:36 and 56:44.

As will be understood the process according to the invention may be practiced within wide limits with respect to parameters such as temperature, pressure and gas composition. However, there are certain limitations of the practicing of the invention. Deposition of carbon is such a limitation. Carbon formation mainly will take part according to the following reactions which regarding energy are referred to 1 bar and 0° C.

$$2CO \rightleftharpoons C + CO_2 \quad \Delta H = -172.24 \text{ kJ/mol} \quad (4)$$

$$CO \rightleftharpoons C + \tfrac{1}{2}O_2 \quad \Delta H = 110.74 \text{ kJ/mol} \quad (5)$$

$$CO_4 \rightleftharpoons C + 2H_2 \quad \Delta H = 74.15 \text{ kJ/mol} \quad (6)$$

Another limitation for practicing the process is that at low temperature a number of metals, including nickel which is used in methanation catalysts, will react with carbon monoxide in the gas while forming metal carbonyls. The tendency to this reaction will increase with increasing concentration of carbon monoxide in the gas. This problem may be partly solved by placing immediately ahead of the methanation catalyst bed another catalyst bed with a catalyst promoting reaction (3) and not containing metals capable of reacting with carbon monoxide.

Therefore, it is convenient to place a bed of a shift catalyst which catalyzes the shift reaction (3) and does not contain iron or nickel, in at least one of the two methanation reactors, i.e. the adiabatic methanation reactor and/or the cooled methanation reactor ahead of the bed of the methanation catalyst, seen in the flow direction of the gas. Such shift catalysts as a rule contain at least two of the metals copper, zinc and chromium, optionally in the form of oxides and optionally on a carrier. It is unimportant for the effect explained which shift catalyst there is employed only it does not contain metals forming metal carbonyls.

The invention also relates to a plant for carrying out the process described. According to the invention, such plant comprises, in combination at least one adiabatic methanation reactor, at least one coold methanation reactor, a feed line for feed gas, means for dividing the feed gas into a first and a second feed gas part stream, means for feeding the first feed gas part stream into the adiabatic methanation reactor, means for discharging partly methanated gas from the adiabatic methanation reactor and means for cooling that partly methanated gas, means for mixing the cooled, partly methanated gas from the adiabatic reactor with the second feed gas part stream, means for feeding the thus-combined stream into the cooled methanation reactor, and means for discharging the reacted gas from the cooled methanation reactor as a product gas stream.

In a preferred embodiment of the plant according to the invention, it comprises means for dividing the effluent from the cooled methanation reactor into a product gas stream and a recycle gas stream, and means for recycling the recycle gas stream and mixing it with the first feed gas stream upstream of its introduction into the adiabatic methanation reactor. Preferably, means for cooling the recycle gas is attached to the means for recycling it.

In a preferred embodiment, utilizing the heat evolved in a very economical manner, the plant comprises a steam drum connected to a line for feeding water, optionally preheated, thereto, and lines for feeding water under pressure from the steam drum to the cooling means in the cooled methanation reactor, operating with boiling water under pressure as coolant, and means for recycling said water to the steam drum; means for feeding saturated steam generated in the steam drum as coolant to the means for cooling partly reacted gas from the methanation reactor; and means for discharging superheated steam generated in the last-mentioned exchanger for use elsewhere.

DETAILED DESCRIPTION OF THE DRAWING

As shown in FIG. 1, which shows a flow diagram for a plant for carrying out the invention in which no part of the gas emanating from the cooled methanation reactor is recycled to the first feed gas part stream, the stream of fresh feed gas conveyed via line 1 from a gasification and purification step not shown is subdivided into two streams 2 and 3 which are conducted to an adiabatic methanation reactor 20 and a cooled methanation reactor 30, respectively. If the feed gas contains considerable amounts of carbon monoxide, it is convenient if the gas through the adiabatic reactor first passes a catalyst bed 21 containing a catalyst which only catalyzes the shift reaction (3). Thereafter the gas is passed through a catalyst bed 22 containing a methanation catalyst. The hot gas leaves reactor 20 via a line as stream 4 and after cooling in a heat exchanger 50 is united with part stream 3 and forms an inlet stream 5 to cooled methanation reactor 30. If desired, there may be several cooled methanation reactors in series. In this reactor the gas stream first passes through a catalyst bed 31 containing a shift catalyst which only catalyzes reaction (3). However, this may normally be omitted in cases where the content of carbon monoxide is low. Thereafter the gas passes a methanation catalyst which in FIG. 1 is placed within a tube 32 surrounded by cooling medium in a vessel 33. The gas is discharged via line 6 from reactor 30. Gas stream 6 from cooled reactor 30 may be treated in many different ways according to the planned use thereof. In FIG. 1 it is intimated that it can be dried by condensing steam out by chilling at 25° C. in a condenser 80 and subsequently be led away as finished product gas via line 10.

FIG. 1 shows a preferred use of the heat of reaction evolved. Cooling medium 33 in reactor 30 is boiling water under pressure which over lines 12 and 13 is in continuous connection with a steam drum 70. Boiler feed water, optionally preheated, is supplied via line 11 to the steam drum and the saturated steam is conducted from the steam drum via line 14 through heat exchanger 50 where it is superheated by the hot gas stream 4 from the adiabatic reactor. The superheated steam thereby generated leaves heat exchanger 50 via line 15. This superheated steam may be relaxed in known manner in a turbine driving an electricity generator.

Figure 2:
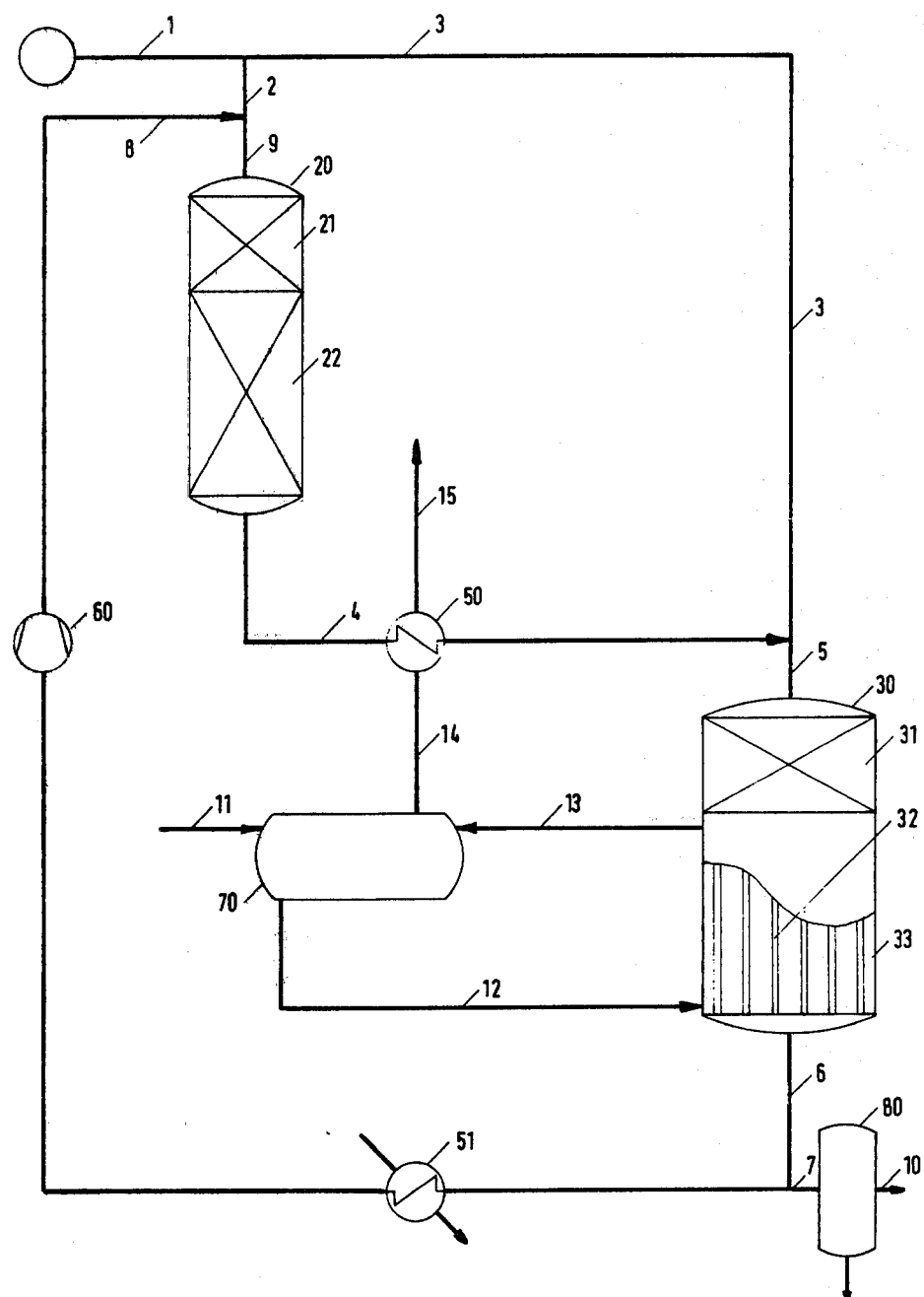

FIG. 2 shows an embodiment with recycling of part of the product gas. Gas stream 6 from cooled methanation reactor 30 is divided into a recycle stream 8 and a stream 7 for further treatment or use as product gas. Recycle stream 8, which is optionally cooled in a heat exchanger 51, is united by the aid of a compressor 60 with feed gas part stream 2 and together with this fed to adiabatic methanation reactor 20 as combined stream 9. The compressor 60 may if desired be replaced by an ejector driven by feed gas part stream 2. The recycle stream 8 contains considerable amounts of water (as steam) and methane and thereby serves at limiting the temperature increase in the adiabatic methanation reactor 20.

EXAMPLES

The practical utilization of the process according to the invention will be illustrated in the following with some calculation examples placed in a Table and set up with a view to carrying out the methanation in a plant constructed in principle as or almost as those just described. The pressure stated in the Table are all gauge pressures.

The Examples have in common that the calculations have been conducted under the assumption that the methanation catalyst in the cooled reactor is placed inside the tubes and that the surrounding cooling medium is boiling water.

The possibilities of utilizing the invention has been demonstrated by eight different Examples which are random examples of the many possible embodiments of the invention and thus not should be construed as limitations therein. Example 1 concerns the embodiment without recycling, i.e. carried out in a plant according to FIG. 1, whereas Examples 2–8 all represent methanations carried out with recycling, i.e. according to the flow diagram shown in FIG. 2. From the Table the various operation parameters can be read. Amongst the most interesting features of the Examples the attention can here be drawn to the feed gas compositions. Examples 1–4 show a feed gas composition which will be characteristic for a methanation plant used in connection with transport of energy from a nuclear reactor. By the aid of heat from the nuclear reactor methane is decomposed by steam reforming into a carbon oxiderich gas; this gas via pipe-lines is conveyed to a site where the energy is to be used, and here the heat of reaction is liberated by methanation. In Example 4 it can also be emphasized that the recycle stream 8 is not cooled, i.e. that the heat exchanger 51 can be omitted which means a simplification of the plant. The feed gas stream in Example 5 contains mainly hydrogen and carbon monoxide in the stoichiometric proportion 3:1. In Examples 6 and 7 the feed gas contains a certain amount of nitrogen. In Example 8 there is an excess of carbon oxides relative the content of hydrogen.

It has particular interest to note the recycle ratio, i.e. the ratio of recycle gas stream 8 conducted from the cooled reactor to admixture with part stream q on one hand, and the amount of freshly added feed gas, i.e. stream 1 on the other hand. In the Examples shown this recycle ratio is from 0.15 to 0.65 whereas in known methanation processes the amount of recycle gas normally is greater, frequently much greater than the amount of freshly added gas. The recycle ratio may be up to several hundred and e.g. in the Examples in British published patent application No. 2,018,818, where one did attempt at keeping it low, it is of the order of magnitude of 3. The drastical reduction of the recycle ratio achieved is a surprising result of the combination of an adiabatic and a cooled methanation reactor and is highly advantageous since it very substantially reduces the compression work in compressor 60 and other energy consumption which is not utilized and therefore must be characterized as waste or loss.

TABLE

| Example No. | 1 | 2 | 3 | 4 | 5 | 6 | 7 | 8 |
|---|---|---|---|---|---|---|---|---|
| Feed gas stream 1: | | | | | | | | |
| Velocity Nm$^3$/h | 100,000 | 100,000 | 100,000 | 100,000 | 100,000 | 100,000 | 100,000 | 100,000 |
| Pressure kg/cm$^2$ | 42.3 | 42.3 | 42.3 | 42.3 | 42.3 | 30 | 75 | 75 |
| Temperature °C. | 300 | 220 | 275 | 300 | 250 | 300 | 300 | 300 |
| Composition % by vol. H$_2$ | 64.13 | 64.13 | 64.13 | 64.13 | 74.92 | 61.08 | 61.08 | 57.73 |
| % by vol. CO | 11.29 | 11.29 | 11.29 | 11.29 | 24.98 | 10.75 | 10.75 | 10.16 |
| % by vol. CO$_2$ | 7.59 | 7.59 | 7.60 | 7.60 | 0 | 7.23 | 7.23 | 16.82 |
| % by vol. CH$_4$ | 16.87 | 16.87 | 16.88 | 16.88 | 0 | 16.09 | 16.08 | 15.20 |
| % by vol. H$_2$O | 0.10 | 0.10 | 0.10 | 0.10 | 0.10 | 0.10 | 0.10 | 0.09 |
| % by vol. inerts (N$_2$ etc.) | 0.00 | 0.00 | 0.00 | 0.00 | 0.00 | 4.75 | 4.76 | 0.00 |
| Part feed gas stream 2: | | | | | | | | |
| Velocity Nm$^3$/h | 64,099 | 56,905 | 54,023 | 55,443 | 56,880 | 52,511 | 46,606 | 44,070 |
| Pressure, temperature and composition as 1 | | | | | | | | |
| Part feed gas stream 3: | | | | | | | | |
| Velocity Nm$^3$/h | 35,901 | 43,095 | 45,977 | 44,556 | 43,119 | 44,789 | 53,394 | 55,920 |
| Pressure, temperature and composition as 1 | | | | | | | | |
| Combined feed gas stream 9 to adiabatic reactor: | | | | | | | | |
| Velocity Nm$^3$/h | —(x) | 71,471 | 81,847 | 75,443 | 122,255 | 95,998 | 94,687 | 86,607 |
| Pressure kg/cm$^2$ | — | 42.3 | 42.3 | 42.3 | 42.3 | 30 | 75 | 75 |
| Temperature °C. | — | 220 | 250 | 308 | 250 | 300 | 300 | 300 |

(x)identical to 2

| | 1 | 2 | 3 | 4 | 5 | 6 | 7 | 8 |
|---|---|---|---|---|---|---|---|---|
| Composition % by vol. H$_2$ | — | 51.48 | 43.03 | 47.67 | 36.01 | 34.44 | 30.86 | 29.60 |
| % by vol. CO | — | 8.99 | 7.45 | 8.30 | 11.62 | 5.88 | 5.29 | 5.17 |
| % by vol. CO$_2$ | — | 6.15 | 5.20 | 5.73 | 0.29 | 4.23 | 3.78 | 16.04 |
| % by vol. CH$_4$ | — | 29.94 | 30.28 | 27.33 | 26.12 | 32.33 | 34.48 | 35.54 |
| % by vol. H$_2$O | — | 8.46 | 14.04 | 10.97 | 25.96 | 17.19 | 19.51 | 17.65 |
| % by vol. inerts | — | 0.00 | 0.00 | 0.00 | 0.00 | 5.93 | 6.08 | 0.00 |
| Outlet stream 4 from adiabatic reactor: | | | | | | | | |
| Velocity Nm$^3$/h | 52,651 | 58,971 | 69,496 | 64,329 | 106,328 | 85,043 | 83,491 | 75,638 |
| Pressure kg/cm$^2$ | 41.8 | 41.8 | 41.8 | 41.8 | 41.8 | 29.5 | 74.5 | 74.5 |
| Temperature °C. | 799 | 700 | 650 | 700 | 650 | 600 | 600 | 600 |
| Composition % by vol. H$_2$ | 39.97 | 27.73 | 22.31 | 27.73 | 23.20 | 18.69 | 13.65 | 9.06 |
| % by vol. CO | 8.46 | 3.33 | 1.77 | 3.33 | 1.62 | 1.06 | 0.53 | 1.75 |
| % by vol. CO$_2$ | 3.67 | 4.47 | 4.28 | 4.47 | 4.59 | 3.91 | 3.05 | 15.29 |
| % by vol. CH$_4$ | 31.45 | 40.70 | 44.46 | 40.70 | 37.50 | 42.94 | 45.80 | 43.37 |
| % by vol. H$_2$O | 16.45 | 23.77 | 27.18 | 23.77 | 33.09 | 26.71 | 30.07 | 30.53 |
| % by vol. inerts | 0.00 | 0.00 | 0.00 | 0.00 | 0.00 | 6.69 | 6.90 | 0.00 |
| Combined feed gas stream 5 to cooled reactor: | | | | | | | | |
| Velocity Nm$^3$/h | 88,552 | 102,066 | 115,473 | 108,885 | 149,447 | 132,532 | 136,805 | 134,490 |
| Pressure kg/cm$^2$ | 41.3 | 41.3 | 41.3 | 41.3 | 41.3 | 29.0 | 74.0 | 74.0 |
| Temperature °C. | 331 | 301 | 323 | 331 | 326 | 334 | 332 | 330 |
| Composition % by vol. H$_2$ | 49.79 | 43.09 | 38.95 | 42.63 | 38.13 | 33.89 | 32.16 | 29.76 |
| % by vol. CO | 9.62 | 6.69 | 5.56 | 6.59 | 8.36 | 4.53 | 4.52 | 5.33 |
| % by vol. CO$_2$ | 5.26 | 5.78 | 5.60 | 5.74 | 3.26 | 5.10 | 4.68 | 15.94 |
| % by vol. CH$_4$ | 25.55 | 30.65 | 33.49 | 30.96 | 26.68 | 33.31 | 34.21 | 31.38 |
| % by vol. H$_2$O | 9,78 | 13.78 | 16.4 | 14.08 | 23.57 | 17.17 | 18.37 | 17.59 |
| % by vol. inerts | 0.00 | 0.00 | 0.00 | 0.00 | 0.00 | 6.00 | 6.06 | 0.00 |
| Outlet stream 6 from cooled reactor: | | | | | | | | |
| Velocity Nm$^3$/h | 62,937 | 77,503 | 90,761 | 82,937 | 115,976 | 108,304 | 112,667 | 108,734 |
| Pressure kg/cm$^2$ | 40.3 | 40.3 | 40.3 | 40.3 | 40.3 | 28.0 | 73.0 | 73.0 |
| Temperature °C. | 330 | 330 | 330 | 330 | 330 | 330 | 330 | 310 |
| Composition % by vol. H$_2$ | 2.6 | 2.06 | 2.06 | 2.08 | 2.17 | 2.27 | 1.56 | 0.45 |
| % by vol. CO | 0.001 | 0.001 | 0.001 | 0.001 | 0.001 | 0.001 | 0.000 | 0.005 |
| % by vol. CO$_2$ | 0.55 | 0.55 | 0.55 | 0.56 | 0.54 | 0.60 | 0.43 | 15.23 |
| % by vol. CH$_4$ | 56.35 | 56.27 | 56.28 | 56.26 | 48.83 | 51.94 | 52.31 | 48.48 |
| % by vol. H$_2$O | 41.11 | 41.11 | 41.10 | 41.10 | 48.46 | 37.84 | 38.33 | 35.84 |
| % by vol. inerts | 0.00 | 0.00 | 0.00 | 0.00 | 0.00 | 7.34 | 7.37 | 0.00 |
| Product gas stream 7 to further treatment: | | | | | | | | |
| Velocity Nm$^3$/h | —(x) | 62,937 | 62,937 | 62,937 | 50,601 | 64,817 | 64,586 | 66,205 |

(x)identical to 6

| | 1 | 2 | 3 | 4 | 5 | 6 | 7 | 8 |
|---|---|---|---|---|---|---|---|---|
| Recycle stream 8: | | | | | | | | |
| Velocity Nm$^3$/h | — | 14,566 | 27,824 | 20,000 | 65,375 | 43,487 | 48,081 | 42,529 |
| Pressure kg/cm$^2$ | — | 42.3 | 42.3 | 42.3 | 42.3 | 30 | 75 | 75 |
| Temperature °C. | — | 220 | 220 | 330 | 250 | 300 | 300 | 300 |
| Composition as 6 | | | | | | | | |
| Dried product stream 10: | | | | | | | | |
| Velocity Nm$^3$/h | 37,093 | 37,093 | 37,093 | 37,093 | 26,097 | 40,338 | 39,847 | 42,496 |
| Pressure kg/cm$^2$ | 38.3 | 38.3 | 38.3 | 38.3 | 38.3 | 26.0 | 71.0 | 71.0 |
| Temperature °C. | 25 | 25 | 25 | 25 | 25 | 25 | 25 | 25 |
| Composition % by vol. H$_2$ | 3.50 | 3.50 | 3.50 | 3.54 | 4.21 | 3.64 | 2.53 | 0.70 |
| % by vol. CO | 0.002 | 0.002 | 0.002 | 0.002 | 0.002 | 0.002 | 0.001 | 0.01 |

TABLE-continued

| Example No. | 1 | 2 | 3 | 4 | 5 | 6 | 7 | 8 |
|---|---|---|---|---|---|---|---|---|
| % by vol. $CO_2$ | 0.95 | 0.95 | 0.94 | 0.95 | 1.06 | 0.97 | 0.69 | 23.73 |
| % by vol. $CH_4$ | 95.47 | 95.47 | 95.48 | 95.43 | 94.65 | 83.47 | 84.80 | 75.62 |
| % by vol. $H_2O$ | 0.08 | 0.08 | 0.08 | 0.08 | 0.08 | 0.12 | 0.04 | 0.04 |
| % by vol. inerts | 0.00 | 0.00 | 0.00 | 0.00 | 0.00 | 11.80 | 11.94 | 0.00 |
| Recycle ratio: | | | | | | | | |
| Velocity (8)/Velocity (1) | — | 0.15 | 0.28 | 0.20 | 0.65 | 0.43 | 0.48 | 0.43 |

I claim:

1. A process for preparing a methane-rich gas mixture by catalytic treatment at elevated temperature and pressure of a feed gas which contains hydrogen as the predominant component, is rich in carbon oxides and optionally contains gases selected from the class consisting of nitrogen and the inert gases, comprising the steps of
   (a) dividing the feed gas into two streams, viz. a first feed gas part stream comprising 30-70% by volume of the total feed gas stream and a second feed gas part stream comprising the remainder of the feed gas,
   (b) subjecting the first feed gas part stream to a catalytic methanation in at least one adiabatic methanation reactor containing a methanation catalyst,
   (c) cooling the effluent gas stream from the adiabatic methanation reactor to 250°-400° C. with saturated steam produced in the cooled methanation reactor according to step (e),
   (d) mixing the cooled effluent stream of step (c) with the second feed gas part stream to form a combined stream,
   (e) subjecting the combined stream from step (d) to a catalytic methanation in at least one methanation reactor cooled by water under production of saturated steam and, containing a methanation catalyst, and
   (f) recovering at least part of the effluent from the cooled methanation reactor as a product gas.

2. A process as claimed in claim 1, wherein the effluent from the cooled methanation reactor is divided into a product gas stream and a recycle stream, the recycle stream being mixed with the first feed gas part stream before its conveyance to the adiabatic methanation reactor, the ratio recycle stream to first feed gas part stream being between 0.05:1 and 1.5:1.

3. A process as claimed in claim 2, wherein the recycle stream is cooled to 200°-400° C. before its admixture with the first feed gas part stream.

4. A process as claimed in claim 2, wherein the ratio recycle stream to first feed gas part stream is between 0.1:1 and 0.9:1.

5. A process as claimed in claim 1, wherein the same methanation catalyst is used in the adiabatic methanation reactor and the cooled methanation reactor.

6. A process as claimed in claim 1, wherein a catalyst not containing iron and nickel and catalyzing the shift reaction $$CO + H_2O \rightleftharpoons CO_2 + H_2$$

is placed in at least one of the methanation reactors ahead of the methanation catalyst, seen in the direction of the gas flow.

* * * * *